United States Patent
Yehiely et al.

(10) Patent No.: US 12,226,268 B2
(45) Date of Patent: Feb. 18, 2025

(54) ERGONOMIC PELVIC SUPPORT PLATFORM

(71) Applicants: Nili Yehiely, Zur Yigal (IL); Moty Biran, Petah Tikva (IL)

(72) Inventors: Nili Yehiely, Zur Yigal (IL); Moty Biran, Petah Tikva (IL)

(73) Assignee: RESTAND MEDIC LTD., Tzur Yigal (IL)

( * ) Notice: Subject to any disclaimer, the term of this patent is extended or adjusted under 35 U.S.C. 154(b) by 505 days.

(21) Appl. No.: 17/613,103

(22) PCT Filed: May 26, 2020

(86) PCT No.: PCT/IL2020/050573
§ 371 (c)(1),
(2) Date: Nov. 22, 2021

(87) PCT Pub. No.: WO2020/240545
PCT Pub. Date: Dec. 3, 2020

(65) Prior Publication Data
US 2022/0218112 A1   Jul. 14, 2022

Related U.S. Application Data

(60) Provisional application No. 62/853,065, filed on May 27, 2019.

(51) Int. Cl.
*A61B 90/60*   (2016.01)
*A47C 9/02*   (2006.01)

(52) U.S. Cl.
CPC .............. *A61B 90/60* (2016.02); *A47C 9/025* (2013.01)

(58) Field of Classification Search
CPC .............................. A61B 90/60; A47C 9/025
USPC ....................................................... 248/125.1
See application file for complete search history.

(56) References Cited

U.S. PATENT DOCUMENTS

| | | | |
|---|---|---|---|
| 3,754,787 A | 8/1973 | Garber | |
| 5,199,763 A * | 4/1993 | Wilder | A47C 9/025 297/15 |
| 6,224,154 B1 | 5/2001 | Stoki | |
| 9,968,195 B2 * | 5/2018 | Sheinkop | A47C 7/006 |
| 2016/0000631 A1 | 1/2016 | Becker | |
| 2018/0303575 A1 * | 10/2018 | Nardo | A61B 90/60 |

FOREIGN PATENT DOCUMENTS

DE   4244657 A1   10/1993

* cited by examiner

*Primary Examiner* — Todd M Epps
(74) *Attorney, Agent, or Firm* — Dr. Hanan Farber Patent Agent Ltd.

(57) ABSTRACT

An ergonomic device for supporting a user during prolonged standing including: a main support, a base attachable to a distal point of the main support, a pelvic support attachable to the main support at a proximal point, a secondary support attachable between an intermedial point of the main support and the base. The user is supported from the front by the pelvic support while standing on the base.

19 Claims, 3 Drawing Sheets

ERGONOMIC PELVIC SUPPORT PLATFORM

BACKGROUND

1. Technical Field

The present invention relates to a device for ergonomic support.

2. Description of Related Art

Certain professions require prolonged standing in a relatively constant position, while manipulating tools of the profession. Prolonged standing may lead to musculoskeletal strain and neurological damage, typically of the neck, shoulder, arm, hand, lower back, pelvis, and foot. The field of ergonomics aims to minimize such damage, by providing optimal support of the human body in a given position, and by improving the grasped areas of tools, to best suit human anatomy. Surgery is an example of one profession which requires prolonged standing, either bent over an operating table (during open surgery), or with arms extended (during laparoscopic surgery). A surgeon may be highly limited in the movements she may make during hours-long surgery. Both the operating table, height and location of viewing monitors, are not as adjustable as ideal, so as to ease or prevent a surgeon's pain during the course of prolonged surgery.

BRIEF SUMMARY

Various ergonomic devices and methods are disclosed herein for an ergonomic device including: a main support, a base attachable to a distal point of the main support, a pelvic support attachable to the main support at a proximal point, a secondary support attachable between an intermedial point of the main support and the base. The user may be supported from the front by the pelvic support while standing on the base. The main support may include overlapping elements and configured for adjustment of distance between the proximal point and the distal point or height of the pelvic support. The main support may include a linear actuator attached to a slidable element configured to adjust position (height) of the pelvic support. A foot pedal or hand switch when pressed is configured to actuate the linear actuator and adjust the position of the pelvic support. The secondary support may include a linear actuator configured for adjustment of an elevational angle of the main support. A foot pedal or hand switch when pressed may actuate the linear actuator and adjust the elevational angle of the main support. The pelvic support may support pelvis of a user from the front during prolonged standing with feet on the base. The pelvic support may include a cushion including memory foam.

BRIEF DESCRIPTION OF THE DRAWINGS

The invention is herein described, by way of example only, with reference to the accompanying drawings, wherein.

Figure 1:
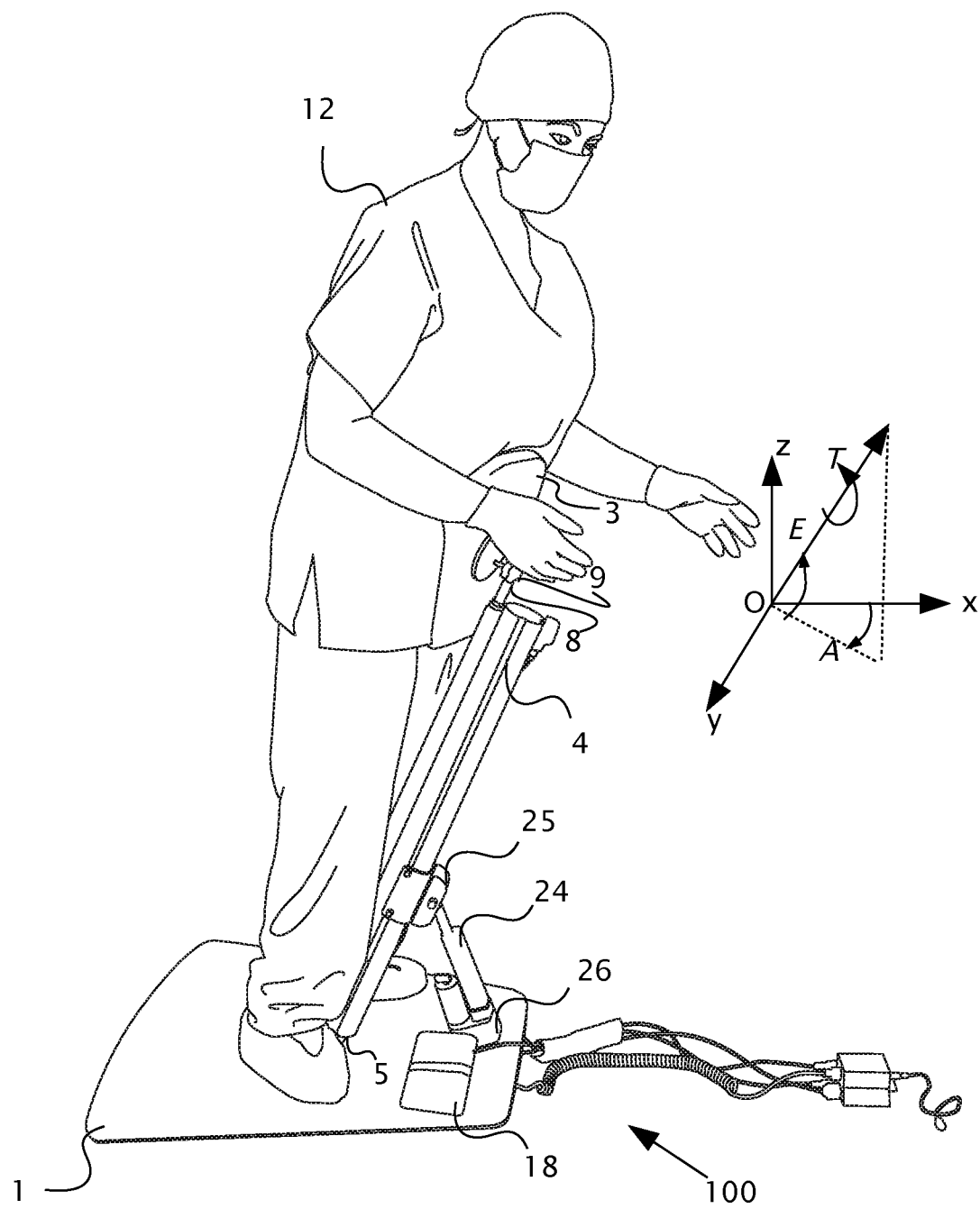
FIG. 1 illustrates an isometric side view of an ergonomic device while in use, according to features of the present invention.

The foregoing and/or other aspects will become apparent from the following detailed description when considered in conjunction with the accompanying drawing figures.

DETAILED DESCRIPTION

Reference will now be made in detail to features of the present invention, examples of which are illustrated in the accompanying drawings, wherein like reference numerals refer to like elements throughout. The features are described below to explain the present invention by referring to the figures.

Figure 3:
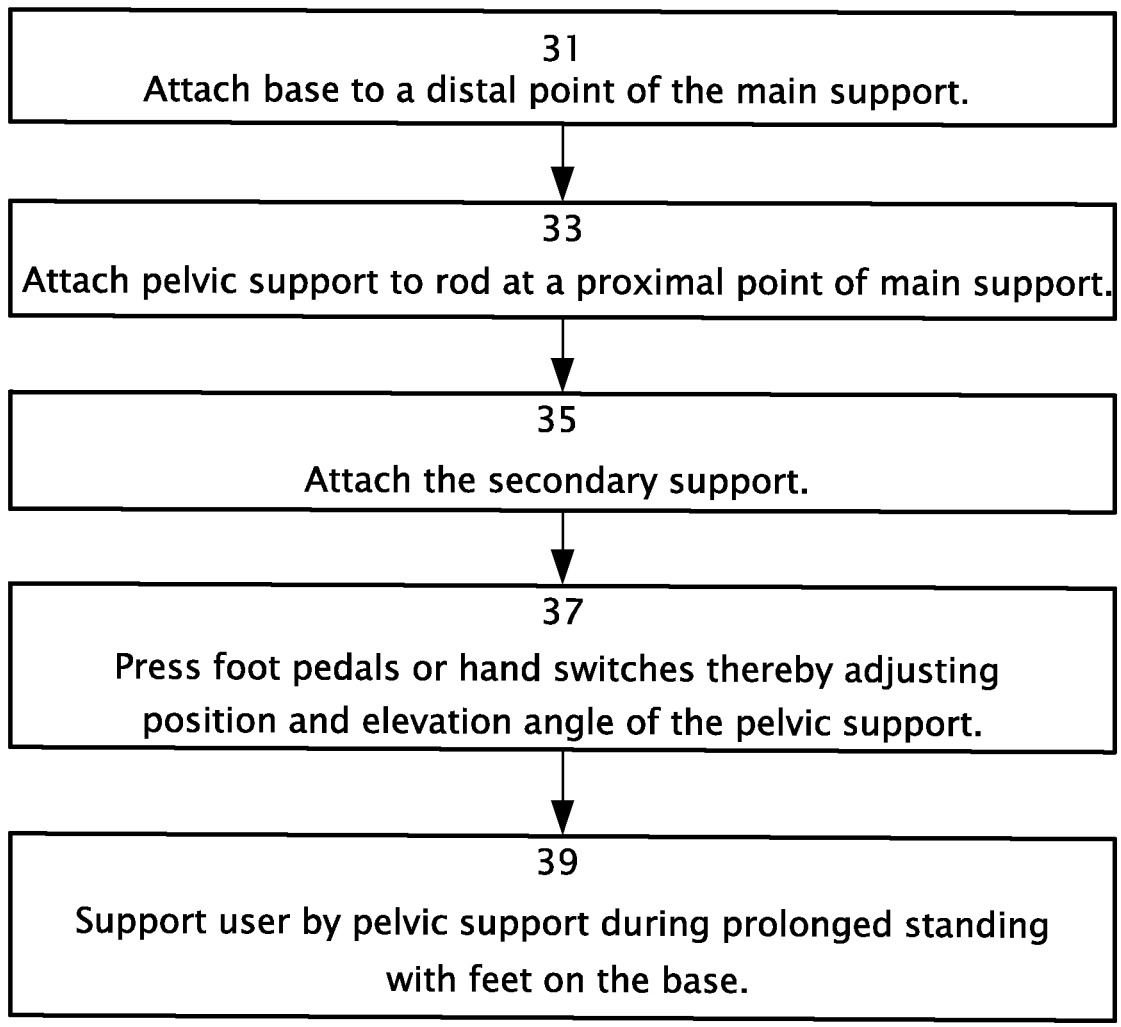
FIG. 3 shows a flowchart of a method, according to features of the present invention.

By way of introduction, aspects of the present invention are directed to provide dynamic and adjustable ergonomic pelvic support, to support a surgeon or other professional during prolonged standing. Embodiments of the present invention are directed to prevent discomfort to a user while she stands in a fixed position during long periods of time, e.g. a lengthy surgical procedure. Moreover, use of embodiments of the present invention provides support in a central portion of the body which assists the user by reducing load and allows for greater ease and precision of manual manipulations. Referring now to the drawings, reference is now made to FIG. 1 which illustrates an isometric side view of ergonomic device 100, according to features of the present invention. Reference is also made to FIG. 3 which is a flow diagram of a method according to features of the present invention. Ergonomic device 100 includes a base 1 upon which a user 12, e.g. surgeon or other professional may stand. Base 1 may be covered with an anti-fatigue mat which tends to absorb shock. A main support bar 4 is attached (step 31) at a distal end to base 1 with a rotatable coupling 5 (not shown) hidden under the mat covering base 1.

A pelvic support with pad 3 attaches (step 33) to a rod 8 which may be slidably attached to support bar 4. In use, pelvic support 3 may be designed to contact and support (step 39) from the front anterior pelvis and/or hip of user 12 as shown. pelvic support 3 may be upholstered for comfort and include springs and/or elastic material to provide shock absorption. A coupling 9 between pelvic support 3 and rod 8 may be rotatable, e.g. ball joint allowing some freedom of orientation along elevation angle E, azimuthal angle A and tilt angle T while user may lean and apply body weight pressure in different directions. Coupling 9 allows pelvic support with pad 3, e.g. rectangular shaped as shown to be oriented horizontally or vertically. A secondary support 24 may attach (step 35) at a distal end to base 1 and at a proximal end to a coupling 25 intermedial on main support bar 4. Secondary support 24 may include a linear actuator 26, e.g. an electrical direct current (DC) motor actuator. Linear actuator 26 may adjust distance between proximal end of secondary support 24, to adjust an elevation angle E of main support bar 4. Main support bar 4 and rod 8 may be telescopic with multiple segments, a segment fitting inside another segment, or otherwise length adjustable, for example by means of an internal linear actuator (not shown). A foot pedal 18 or a hand switch) not shown) may be pressed (step 37) to adjust overall length of support bar 4 and rod 8. Another foot pedal or hand switch, when pressed, may actuate (step 37) linear actuator 26 to adjust overall length of support 24 and to adjust thereby elevation angle E. Foot pedals 18 may activate rocker switches (not shown) which electrically control direct current (DC) motor actuators (only actuator 26 is explicitly shown in FIG. 1). Alternatively, length and elevational angle of main support bar 4 may be manually and/or mechanically adjustable by any known mechanism including pneumatic and/or hydraulic actuation. Azimuthal angle A adjustment and/or height adjustment may be achieved by attaching base 1 to a rotatable and lockable support platform. Utility trays for holding tools and/or arm supports may be attached to support 4 and/or rod 8.

Figure 2:
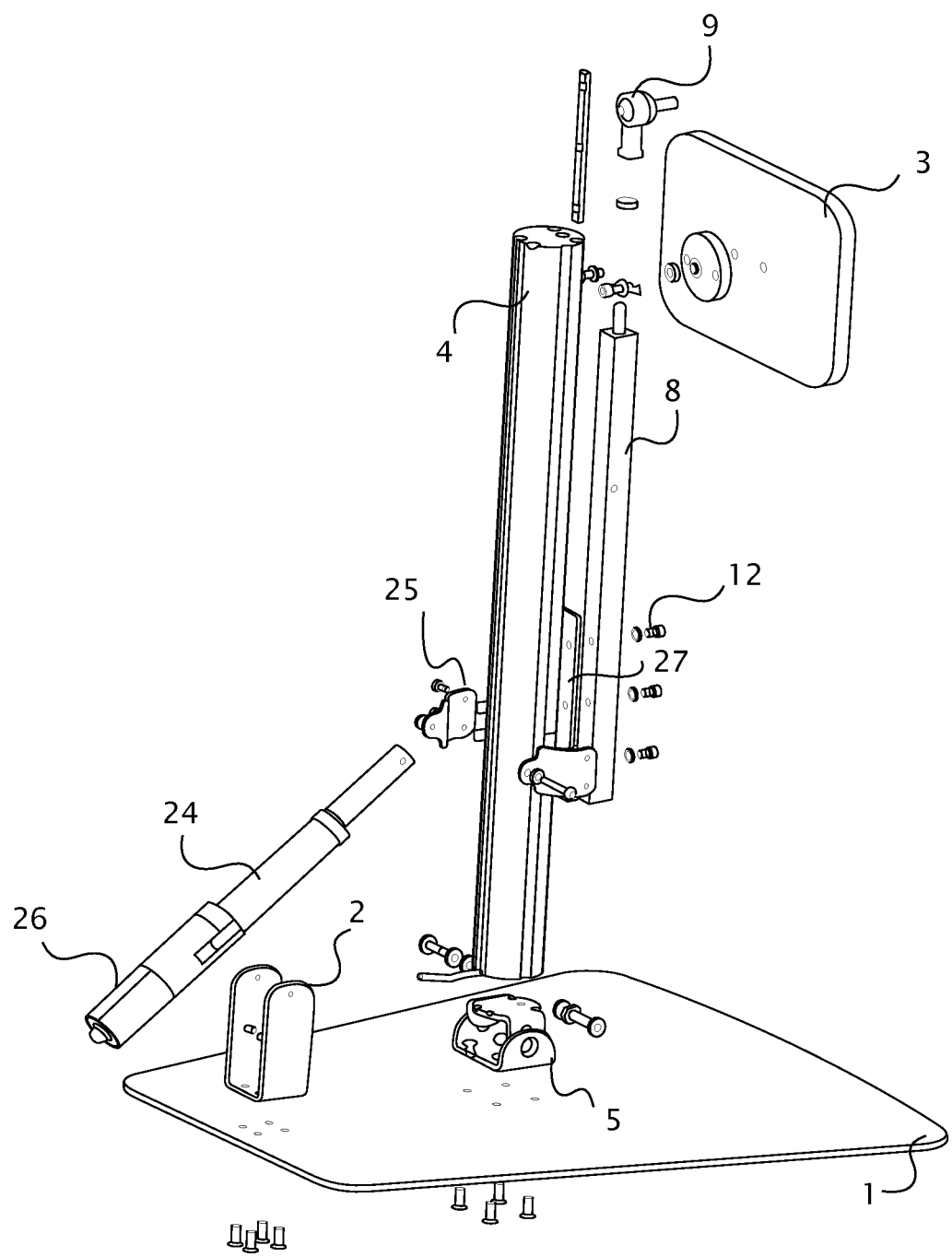
FIG. 2 illustrates an exploded view showing structural features and assembly of an ergonomic device according to features of the present invention.

Reference is now also made to FIG. 2, illustrating an exploded view showing structural features and assembly of ergonomic device 100, according to features of the present invention. Pelvic support 3 may connect via ball joint 9 to rod 8 which at least partially overlaps main support 4. Rod 8 is shown attachable to a slidable element 27 internal to main support 4 using fasteners 12. Pelvic support 3 may by height adjusted by adjusting rod 8 along varying positions along main support 4. A rack and pinion between main support 4 and adjusting rod 8 may be used to adjust pelvic support 3 height during operation. Alternatively, main support 4 may be implemented with Slideway lifter 167 (Baumeister & Schack GmbH Balingen, Germany) which is equipped with an internal electrical linear actuator which may drive slidable element 27. Height adjustment of pelvic support 3 may be performed during operation using pedal 18 (FIG. 1) by driving the internal electrical linear actuator or rack and pinion (not shown).

Clamp 25 may attach the proximal end of secondary support 24 at an intermedial point along main support 4. Distal end of support 24 may attach to base 3 using a C-mount bracket 2 which includes a horizontal axle which provides elevational angle degree of freedom.

Elevational angle E adjustment may be performed with secondary support 24 including a linear actuator such as Actuator KoaxE™ (Baumeister & Schack GmbH, Balingen Germany). Elevational angular adjustment may vary between ninety degrees and seventy degrees. Controllers of the linear electrical actuators may be used are the SYlmini™ manufactured by Baumeister & Schack GmbH of Balingen Germany. Foot pedals 18 may be ELFUSS™ manufactured by Baumeister & Schack GmbH. Balingen Germany. Battery power may be provided by a battery-pack 24 VDC 1.7 AH. Alternatively, power may be provided by power-cords wired to the electrical grid Mechanical components are typically manufactured from stainless steel with anodized coating to prevent corrosion. Some components may be produced from aluminum. Pelvic support 3 may be upholstered using suitable materials, e.g. memory foam that are intended to provide comfort and shock absorption during prolonged contact with user 12.

For use in a sterile environment, such as in surgery, pelvic support 3 and other components used herein, may be wiped down after each use, or may be covered for each use with appropriate materials such as are known in the medical field.

Cartesian coordinate xyz axes as shown in FIG. 1 include a horizontal xy plane horizontal e.g parallel to a worktable, e.g. operating table. Elevation angle E is measured from the horizontal plane xy, and azimuthal angle A is measured from vertical plane xz. Twist angle is about the longitudinal or long axis of support bar 4 and rod 8.

The terms "distal" and "proximal" as used herein are relative to the viewpoint of the user, for example base distal, proximal, intermedial are relative to the user so that distal is near base 1 and proximal is near the pelvic support 3. The "intermedial" as used herein is a point between distal and proximal.

The term "memory foam" as used herein may include but not limited to a viscoelastic polyurethane material with additional chemicals configured to increase its viscosity and density, also known as low-resilience polyurethane foam (LRPu). Memory foam may soften in reaction to body heat, thereby molding to a warm body in a few minutes.

The term "pelvis" as used herein refers to the lower part of the torso located between the abdomen and the legs. The term "hip rest" as used in the priority document (U.S. patent application 62/853,065), filed 27 May 2019) and "pelvic support" as used herein are interchangeable and refers to support in the region of the body near the pelvis. By rotating, e.g. between horizontal and vertical orientations or otherwise adjusting pelvic support 3, different regions of the body may be supported.

The working distance between user 12, e.g. surgeon, and the person/object being operated on or worked on may be decreased by fixing base 1 on a platform, e.g 3-15 centimeters or higher. Depending on height of base 1, elevation angle E in some embodiments may be decreased to less than seventy degrees to an angular range 45-70 degrees, by way of example. Accordingly, pelvic support 3 may be extended to support more perimeter around user's 12 body.

The transitional term "comprising" as used herein is synonymous with "including", and is inclusive or open-ended and does not exclude additional, unrecited elements or method steps. The articles "a", "an" is used herein, such as "a rod" or "a pelvic support" have the meaning of "one or more" that is "one or more rods", "one or more pelvic supports".

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

Although selected features of the present invention have been shown and described, it is to be understood the present invention is not limited to the described features.

The claimed ivention is:
1. An ergonomic device comprising:
   a main support;
   a base attachable to a distal point of the main support;
   a pelvic support attachable to the main support at a proximal point, wherein the proximal point on the main support is opposite the distal point;
   a secondary support attachable between an intermedial point of the main support and the base, wherein the secondary support attaches to the base at a secondary-support-base attachment point, wherein the intermedial point on the main support is between the distal point and the proximal point, wherein the distal point of the main support attaches to the base between a feet-support portion of the base and the secondary-support-base attachment point.

2. The ergonomic device of claim 1, wherein the main support includes a plurality of overlapping elements and configured for adjustment of distance between the proximal point and the distal point.

3. The ergonomic device of claim 1, wherein the main support includes a linear actuator attached to a slidable element configured to adjust position of the pelvic support.

4. The ergonomic device of claim 3, further comprising:
   a foot pedal or hand switch when pressed is configured to actuate the linear actuator and adjust the position of the pelvic support.

5. The ergonomic device of claim 1, wherein the secondary support includes a linear actuator configured for adjustment of an elevational angle of the main support.

6. The ergonomic device of claim 5, further comprising:
a foot pedal or hand switch when pressed is configured to actuate the linear actuator and adjust the elevational angle of the main support.

7. The ergonomic device of claim 1, wherein the pelvic support includes a cushion including memory foam.

8. The ergonomic device of claim 1, wherein the pelvic support is configured to support anterior pelvis of a user during prolonged standing with feet on the feet-support portion of the base.

9. A method of using an ergonomic device including a main support, a base, a pelvic support and a secondary support, the ergonomic device including:
a main support;
a base attachable to a distal point of the main support;
a pelvic support attachable to the main support at a proximal point, wherein the proximal point on the main support is opposite the distal point;
a secondary support attachable between an intermedial point of the main support and the base, wherein the secondary support attaches to the base at a secondary-support-base attachment point, wherein the intermedial point on the main support is between the distal point and the proximal point, wherein the distal point of the main support attaches to the base between a feet-support portion of the base and the secondary-support-base attachment point;
the method comprising:
supporting anterior pelvis of a user by the pelvic support during prolonged standing with feet on the feet-support portion of the base.

10. The method of claim 9, wherein the main support includes a plurality of overlapping elements, the method further comprising:
enabling adjustment of distance between the proximal point and the distal point.

11. The method of claim 9, wherein the main support includes a linear actuator attached to a slidable element, the method further comprising
enabling adjusting position of the pelvic support.

12. The method of claim 11, wherein the ergonomic device includes a foot pedal or a hand switch, the method further comprising:
enabling pressing the foot pedal or the hand switch, actuating thereby the linear actuator and said adjusting the position of the pelvic support.

13. The method of claim 9, wherein the secondary support includes a linear actuator, the method further comprising:
enabling actuating the linear actuator thereby adjusting an elevational angle of the main support.

14. The method of claim 13, further comprising:
enabling pressing the foot pedal or the hand switch, actuating thereby the linear actuator and said adjusting the elevational angle of the main support.

15. The method of claim 9, wherein
the pelvic support is upholstered with a cushion including memory foam.

16. A method of assembly of an ergonomic device, the method comprising:
providing a main support, a base, a pelvic support and a secondary support;
attaching the base to a distal point of the main support;
attaching the pelvic support to the main support at a proximal point; and
attaching the secondary support between an intermedial point of the main support and the base at a secondary-support-base attachment point; wherein the distal point of the main support attaches to the base between a feet-support portion of the base and the secondary-support-base attachment point.

17. The method of claim 16, further comprising adjusting an elevational angle of the main support.

18. The method of claim 16, wherein the main support includes a plurality of overlapping elements, the method further comprising:
enabling adjustment of distance between the proximal point and the distal point.

19. The method of claim 16, wherein the main support includes a linear actuator attached to a slidable element, the method further comprising
enabling adjusting position of the pelvic support.

* * * * *